United States Patent [19]

Surowiec

[11] Patent Number: 5,543,924
[45] Date of Patent: Aug. 6, 1996

[54] METHOD AND APPARATUS FOR EVALUATING PUMMELED GLASS

[75] Inventor: Roman Surowiec, Redford, Mich.

[73] Assignee: Ford Motor Company, Dearborn, Mich.

[21] Appl. No.: 462,325

[22] Filed: Jun. 5, 1995

[51] Int. Cl.[6] .................................. G01N 21/47
[52] U.S. Cl. ................ 356/446; 73/150 A; 356/371
[58] Field of Search .................... 356/371, 446, 356/426; 250/559.16; 73/150 R, 150 A

[56] References Cited

U.S. PATENT DOCUMENTS

| | | | |
|---|---|---|---|
| 2,755,702 | 10/1951 | Cook | 88/14 |
| 3,549,264 | 12/1970 | Christie | 356/210 |
| 4,097,160 | 6/1978 | Yataki et al. | 356/237 |
| 4,344,709 | 8/1982 | Provder et al. | 356/445 |
| 4,393,700 | 7/1983 | Fabian | 73/150 A |
| 4,583,861 | 4/1986 | Yamaji et al. | 356/448 |
| 4,715,718 | 12/1987 | Evans | 356/446 |

*Primary Examiner*—Richard A. Rosenberger
*Attorney, Agent, or Firm*—Lorraine S. Melotik; Roger L. May

[57] ABSTRACT

A novel apparatus and method for evaluating the bonding strength of a laminated glazing is disclosed. A sample of pummeled laminate is rotated while a collimated beam of white light is directed onto the sample at a predetermined angle of incidence. The intensity of light reflected from the sample is measured. The measured intensity is correlated with a standard light intensity corresponding to a known adhesion value.

10 Claims, 5 Drawing Sheets

5,543,924

METHOD AND APPARATUS FOR EVALUATING PUMMELED GLASS

BACKGROUND OF THE INVENTION

1. Field of the Invention

Embodiments of the present invention relate generally to a method and apparatus for evaluating pummeled glass. In one aspect, embodiments of the present invention relate to a method of detecting the nature of light reflected from a sample of pummeled glass and correlating the detected light with light detected from samples of pummeled glass having known pummel adhesion values.

2. Description of Related Art

Common automobile glazing is generally a plural layer laminate having at least one outer transparent glass layer and at least one inner transparent glass layer which are both adhered to an intermediate transparent vinyl or thermoplastic layer. This laminate is often referred to as "safety glass" since the intermediate layer operates to minimize the scattering of glass when the automobile glazing is broken upon impact, i.e. particles of broken glass will generally remain adhered to the intermediate thermoplastic layer rather than being scattered in different directions.

Conventional methods do exist to determine the extent of the bonding strength of a plural layer laminate, such as a paper web to plastic film laminate. See for example U.S. Pat. No. 4,715,718. The standard industry method of evaluating bonding strength within a windshield laminate, however, includes pummeling a test sample of windshield laminate, i.e. impacting a sample cooled to approximately 0° F. with known force so as to break the sample into granular particles, and then visually comparing the test sample itself with samples of pummeled glass having known pummel adhesion values. The operator attempts to visually and, therefore, subjectively match the test sample with a standard pummeled glass sample, and then upon finding a match, assigns the test sample with the pummel value of the matching standard.

One standard set of pummel adhesion values accepted in the industry includes a pummel rating system developed by Monsanto Company (Pummel Adhesion Standards) which rates pummeled glass samples on a scale from 0 to 10 depending upon the nature and extent of adhesion of glass particles to the intermediate thermoplastic layer. Generally, the higher the rating number, the greater the adhesion of the glass particles to the thermoplastic layer.

The standard industry method of evaluating the bonding strength of a windshield laminate, however, includes variability and error often associated with the subjective judgment of the particular individual operator performing the evaluation. The standard industry method, therefore, (1) fails to characterize the quality of pummeled glass samples efficiently and with sufficient repeatability, and (2) fails to minimize the variability and error often associated with a subjective evaluation and comparison of pummel test samples with standard pummel samples. A need therefore exists to develop a method for evaluating pummeled glass which overcomes the deficiencies of the standard industry method.

SUMMARY OF THE INVENTION

The present invention includes a novel apparatus and method for evaluating the nature of pummeled glass and the quality of adhesion between a glass substrate and a vinyl substrate in a pummeled laminate, such as an automobile glazing. In one embodiment, the present invention relates to a method and apparatus for detecting the nature of light reflected from pummeled laminate. A sample of the pummeled laminate is rotated. A collimated beam of light is directed onto the sample at a predetermined angle. The reflected light intensity is then measured as a single measured intensity value or in the form of a plotted scatter intensity profile, and is characteristic of the glass particles and the integrity of the glass/vinyl interface of the pummeled laminate. The measured light intensity is then correlated with light intensity detected from samples of pummeled laminate having known pummel adhesion values. In this way, standard pummel adhesion values can be assigned to test samples without introducing the subjective variability and error often associated with visually comparing the test sample with a standard sample having a known pummel adhesion value.

It is accordingly an object of the present invention to provide a novel method and apparatus for evaluating pummeled glass. It is a further object of the present invention to determine the quality of adhesion between a glass substrate and a vinyl substrate in a laminated automobile glazing. It is a further object of the present invention to characterize the quality of pummeled glass samples efficiently and with sufficient repeatability, and to minimize the variability and error often associated with a manual visual evaluation and comparison of pummel test samples with samples having known pummel adhesion values.

Other objects, features or advantages of the present invention will become apparent from the following description taken in conjunction with the accompanying drawings.

BRIEF DESCRIPTION OF THE DRAWINGS

In the course of the detailed description of certain preferred embodiments to follow, reference will be made to the attached drawings, in which.

DESCRIPTION OF CERTAIN PREFERRED EMBODIMENTS

The principles of the present invention may be applied with particular advantage to obtain a method and apparatus for evaluating pummeled glass, preferred embodiments of which may be seen at FIGS. 1, 2, and 3 which are described more fully below.

Figure 1A:
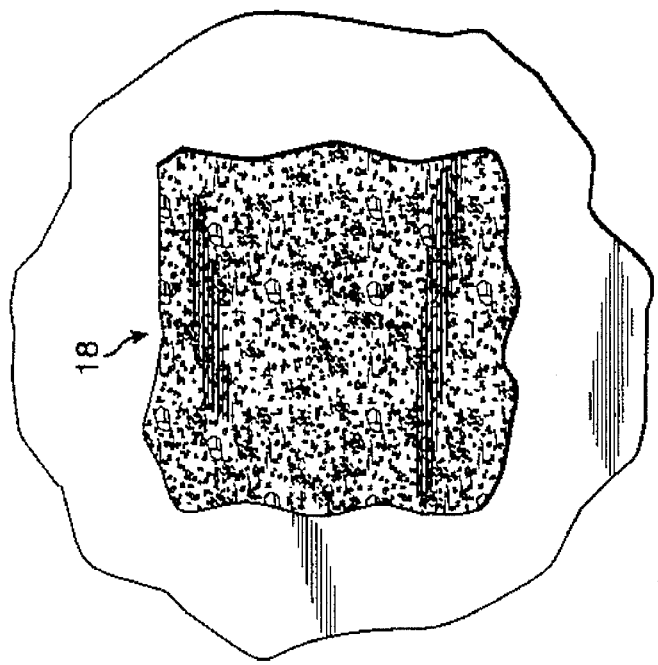
FIG. 1A is a top view of a portion of the pummeled laminate of FIG. 1.
Figure 1:
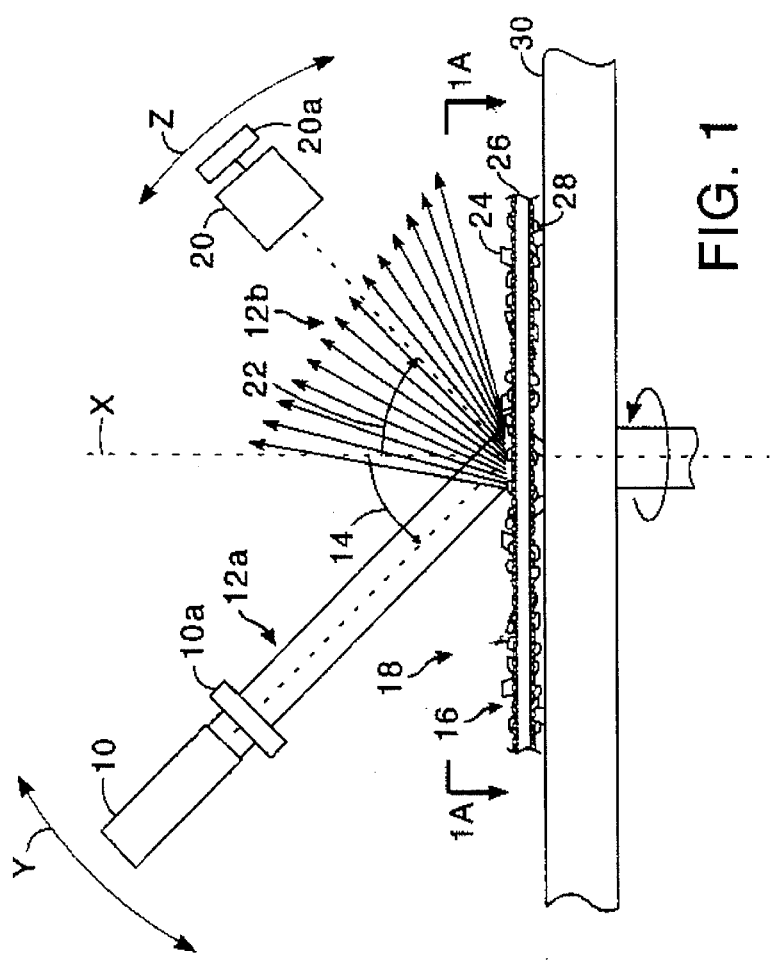
FIG. 1 is a schematic of an apparatus for detecting light which is reflected from the surface of a sample of pummeled laminate.

Referring to FIG. 1, a light source 10 provides a collimated beam of light 12a which is directed at an angle incident 14 to the surface 16 of a sample of pummeled laminate shown generally in cross-section at 18. Detector 20 is positioned at angle of reflectance 22 to receive and measure the intensity of the beam of light 12b which is reflected from the pummeled laminate 18. Due to the granular nature of the pummeled laminate 18, which can be better seen in FIG. 1A, the reflected beam of light 12b is scattered at different angles and is no longer collimated. Pummeled laminate 18 is shown in cross-section in FIG. 1 as having a first glass layer 24, an intermediate layer 26 and a second glass layer 28. The intermediate layer 26 is preferably a vinyl or thermoplastic material which is well known in the art. First glass layer 24 and second glass layer 28 are bonded or adhered to intermediate layer 26 according to principles well known in the art to produce the laminate 18. As can be seen in FIG. 1 and FIG. 1A, the first glass layer 24 and the second glass layer 28 are broken into granulated particles as a result of being pummeled. For the purposes of this application, the term "pummel" is used herein as it is understood by those of ordinary skill in the art and includes impacting a sample of automobile glazing with a hammer at a known force to cause the glazing to break into granulated particles. Since the glass layers 24 and 28 are bonded to the intermediate layer 26, the granulated particles of glass substantially remain adhered to the intermediate layer 24 thereby minimizing scatter of the broken glass.

The light source 10 is positioned relative to normal X of the pummeled laminate 18 to emit light at a desired angle of incidence 14. The detector 20 is correspondingly positioned relative to normal X of the pummeled laminate at angle of reflectance 22 so as to receive the reflected scattered beam of light 12b and to provide a measure of the intensity of the reflected light. Generally, the greater the adhesion of the glass particles to the intermediate layer 26, the more uniform the surface 16 of pummeled laminate 18 will be in terms of surface density of granulated glass particles as opposed to exposed vinyl layer areas, and therefore the greater the light scatter of the reflected scattered beam of light 12b off of the granulated glass particles. The greater the light scatter, the more diffuse the reflected light will be resulting in a lower relative intensity of the scattered light at the measured angle of reflection.

In a preferred embodiment, the light source 10 and the detector 20 are movable relative to normal X, as indicated by arcs Y and Z in FIG. 1, so as to facilitate the detection and measurement of the intensity of reflected light at various desired angles of incidence and angles of reflection which are then plotted to provide an intensity profile of the reflected light for the sample of pummeled laminate 18 being evaluated. According to one embodiment of the present invention, light source 10 is fixed at a desired angle of incidence. Detector 20 then travels in an arc corresponding to a predetermined starting and stopping point centered on the angle of reflection, i.e. ±30° on either side of the angle of reflection, and records the intensity of the reflected scattered beam of light 12b at regular degree intervals. The intensity measurements are then plotted to produce an intensity scatter profile of the reflected light for the desired angle of incidence over the degree range traveled by the detector, such as in FIGS. 4–8.

In a further preferred embodiment, pummeled laminate 18 is secured to turntable 30 and is rotated at a desired speed so that the reflected scattered beam of light 12b will be representative of the average intensity of light reflected from the lo pummeled laminate over the area from which the collimated beam of light 12a is reflected. This aspect of the invention is particularly advantageous in providing intensity readings which are reproducible for a given pummel test sample. It is to be understood that alternate embodiments of the present invention include methods other than simply rotating the test sample to produce an average intensity of light reflected from the pummeled laminate, such as the use of stepper motors to index the sample through a 360° period while taking light intensity measurements at regular degree intervals and then mathematically integrating over the 360° period to arrive at an average intensity.

Figure 2:
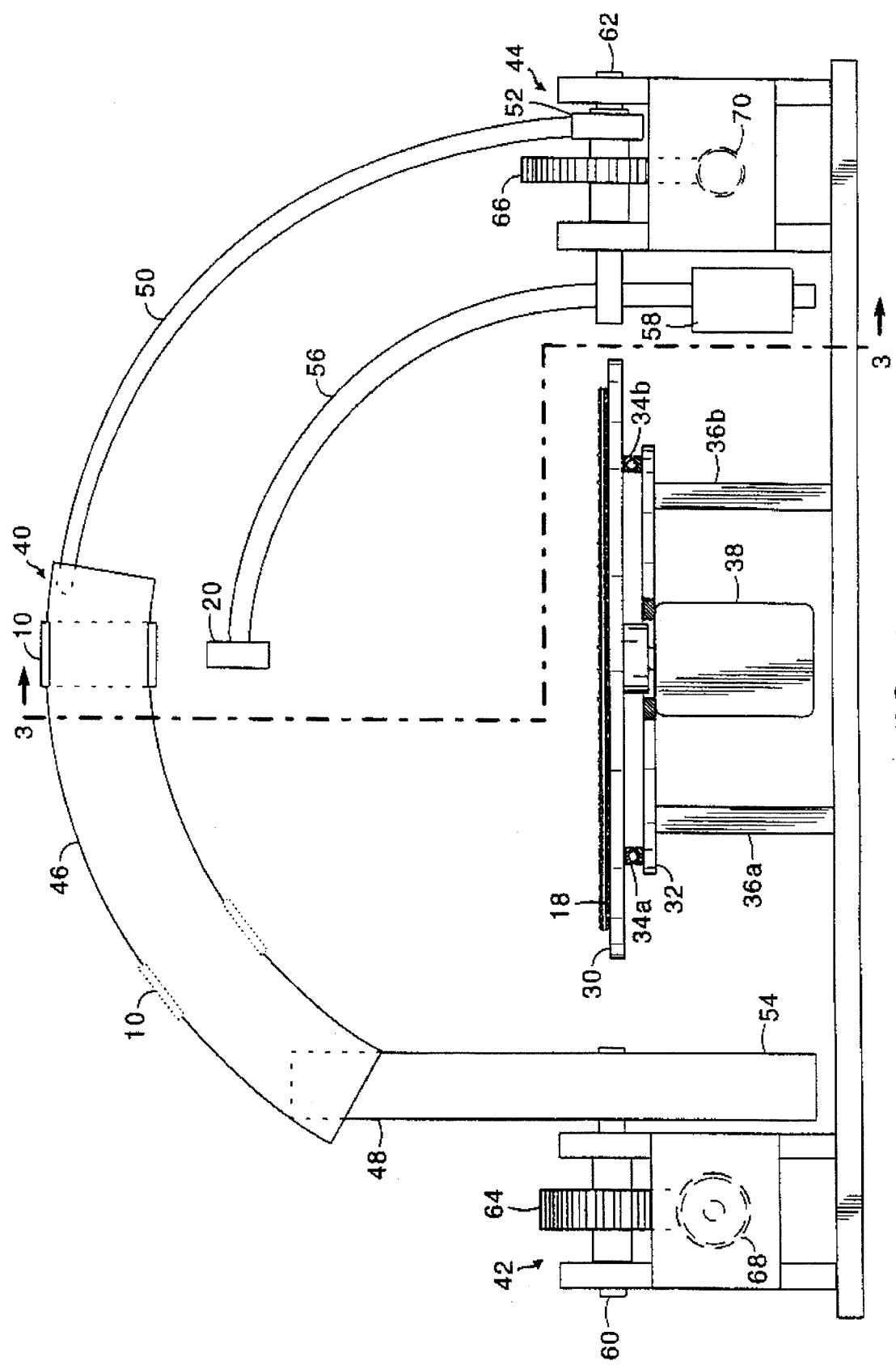
FIG. 2 is a perspective view of one embodiment of an apparatus of the present invention.
Figure 3:
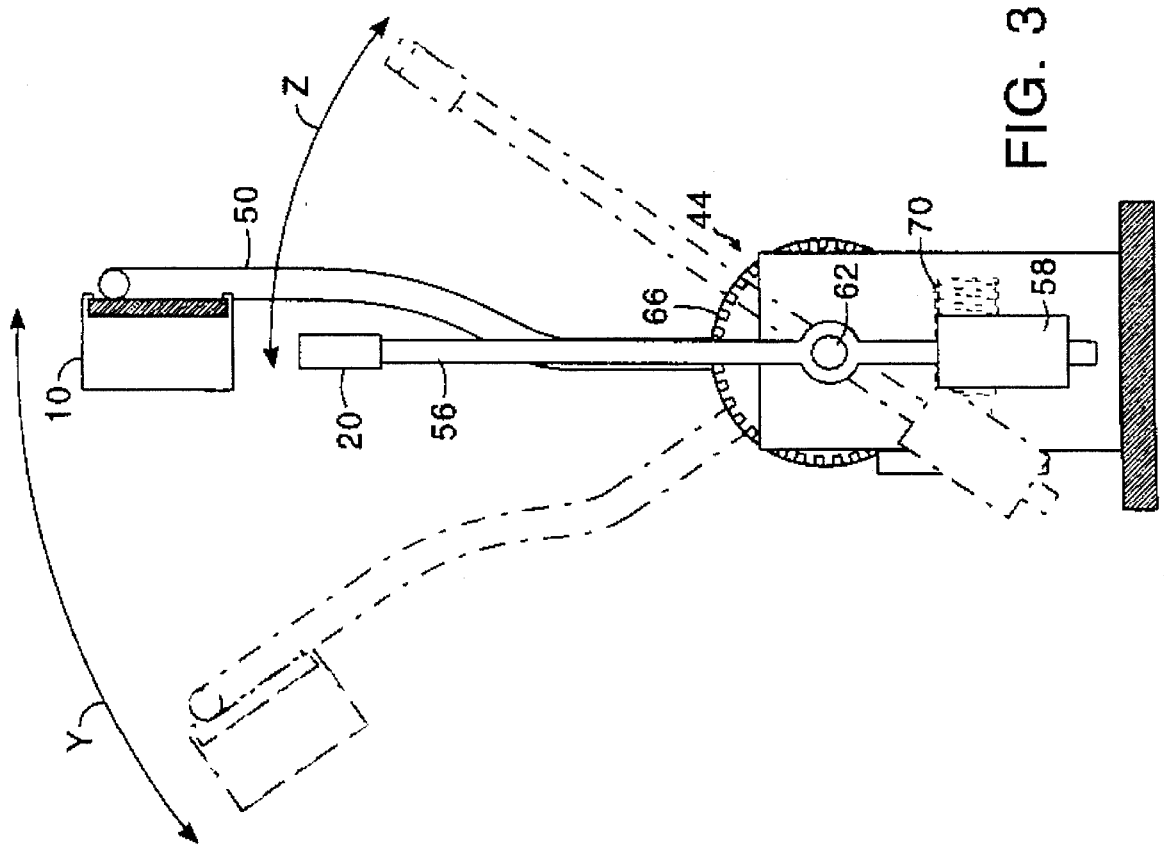
FIG. 3 is a side view of the embodiment of FIG. 1.

Reference will now be made to alternate embodiments of the present invention as shown in FIG. 2 and FIG. 3. For ease of understanding, the same reference numbers will be used to indicate aspects of the invention already disclosed in FIG. 1.

FIG. 2 is a perspective view of an apparatus of the present invention for evaluating pummeled glass. FIG. 3 is a side view of the apparatus of FIG. 2 taken along line 3—3. As can be seen in FIG. 2, a sample of pummeled glass 18 is placed on and secured to turntable 30 which, in turn, is secured to turntable support plate 32 via connectors 34a and 34b. Turntable support plate 32 fixedly rests on support rods 36a and 36b. The turntable assembly depicted in FIG. 2 is a conventional turntable assembly. It is to be understood that alternate turntable embodiments are within the scope of the present invention which perform the function of rotating the sample 18.

Sample 18 is preferably 6 inches by 6 inches and is secured to turntable 30 by standard clamps (not shown) so as to minimize movement and vibration of the sample 18 during rotation of turntable 30. Turntable 30 is preferably round and rotatably attached to motor 38 or other suitable rotation means which is positioned beneath turntable support plate 32. Motor 38 is a conventional motor capable of rotating at various speeds. In a preferred embodiment, motor 38 is capable of rotating the turntable at a speed of between 120 to 240 r.p.m. In an alternate embodiment, the motor 38 is a stepper motor which is useful in the integration method previously described for producing an average light intensity.

Positioned above the sample 18 is light source 10, which is more clearly depicted in FIG. 3, and which is capable by itself or with a converging lens (not shown) of providing a collimated beam of light. Also shown in FIG. 2 is detector 20, also shown in FIG. 3 which is capable of receiving and measuring the intensity of light reflected from the surface of sample 18. In one embodiment of the present invention, the light source 10 and the detector 20 are in the same plane.

In a preferred embodiment, the light source 10 emits a collimated beam of white light, although, the principles of the present invention can also be applied to light sources which emit visible, ultraviolet or infrared radiation so long as corresponding detectors are used to detect the particular type of electromagnetic radiation chosen. In a further preferred embodiment, the wavelength of the light used is not strongly absorbed by the pummeled laminate sample 18 so as to provide greater sensitivity and more accurate intensity measurements by detector 20. The collimated beam of light preferably produces a spot size of approximately 1 inch to 2 inches on the sample 18, although it is to be understood that other spot sizes may be employed in the practice of the present invention. For example, larger spot sizes will generally produce intensity measurements which better represent the average physical characteristics of the sample of pummeled glass being evaluated. It is to be further understood that light source 10 can be any conventional light source known to those skilled in the art, such as a microscope illuminator or a laser. The light source 10 is electrically connected to and powered by a conventional regulated power supply (not shown).

As shown in FIG. 1 and FIG. 3, the light source 10 is mounted to first arched support shown generally at 40 which in turn is pivotally mounted to pivot mechanism shown generally at 42. As shown in FIG. 3, the light source 10 may therefore be advantageously directed at various desired angles of incidence relative to the normal of sample 18. First arched support 40 has rail section 46, along which light source 10 may slidably travel, rotating arm 48 and support rod 50. Rotating arm 48 is pivotally connected to pivot mechanism 42 and support rod 50 is rotatably connected to floating support 52 such that first arched support 40 and light source 10 may pivot through various desired angles of incidence by operation of pivot mechanism 42. Light source 10 is slidably attached to rail section 46 so as to allow light to be directed to the surface of pummel sample 18 from a plane different from the detector 20 and from which intensity measurements may be taken. Rotating arm 48 is equipped with counter weight 54 to aid in the pivoting motion of first arched support 40.

Similarly, detector 20 is mounted to second arched support 56 which in turn is pivotally mounted to pivot mechanism 44 such that second arched support 56 and detector 20 may pivot through various desired angles of reflection by operation of pivot mechanism 44. Second arched support 56 is equipped with counter weight 58 to aid in the pivoting motion of detector 20.

Pivot mechanisms 42 and 44 are shown in FIGS. 2 and 3 as being conventional motor driven gear based pivot mechanisms with pivot pins 60 and 62, first gears 64 and 66, and second gears 68 and 70, respectively. It is to be understood that alternate pivot mechanism assemblies are within the scope of the present invention which perform the function of pivoting first arched support 40 and second arched support 56.

Preferably the light source 10 pivots through an arc of between 0° to 90° relative to normal X while the detector 20 pivots through an arc of between −10° to 190° relative to the surface of sample 18 to provide a maximum number of intensity readings at various desired angles of incidence and angles of reflection. Additionally, pivot mechanism 44 also serves to rotate detector 20 through an arc corresponding to a predetermined starting and stopping point centered on the angle of reflection, i.e. ±30° on either side of the angle of reflection which is determined mathematically from the desired angle of incidence. In this manner, multiple intensity readings may be taken to develop an intensity scatter profile for the pummel sample at a given angle of incidence.

The detector 20 may be any conventional detector suitable for receiving and measuring the intensity of the reflected light. A detector useful in the practice of the present invention includes a UDT™ silicon detector with a photometric filter and with a 1 inch focusing lens. The detector 20, in turn, is connected to a UDT™ model 40X Opto-meter photometer with the output connected to a FLUKE™ 77 digital voltmeter. In a preferred embodiment, the intensity measurements are computerized according to standard methods and may then be plotted or stored for future use or analysis.

As shown in FIG. 1, the angle of incidence 14 and the angle of reflection 22 are measured with respect to a normal X to the surface of sample 18. The angle of incidence 14 of the light source directed upon the surface 16 of sample 18 is generally about 0° to 90°, preferably 10° to 90°, more preferably, 20° to 70°, and most preferably, 25° to 60°.

The use of a single detector 20, as depicted in FIG. 2, for measuring the intensity of the reflected scattered light is advantageous since such detectors whether photoconductive, photogalvanic, photoelectric, etc, are known to change in their sensitivity with time. Therefore use of a single detector will provide greater reliability and consistency of light intensity data. An alternate embodiment of the present invention, however, includes the use of a multiple number of detectors with each detector measuring the intensity of the reflected scattered light 12b at a preset position. The intensity measurements may then be plotted to produce an intensity scatter profile.

Referring to FIG. 1, additional alternate embodiments of the present invention include the use of a modulator 10a to modulate the collimated beam of light 12a emitted from the light source 10 to assure that the reflected scattered beam of light 12b detected by detector 20 will not be affected by extraneous light present in the environment. Where a modulator of the collimated light is utilized prior to directing the light onto the surface 16 of the sample 18, it is desirable to use an amplifier 20a which is tuned to the modulator frequency. The amplifier 20a, which is electrically positioned after the detector 20, ensures that only the detector output signals corresponding to the modulated portion of the reflected scattered beam of light 12b is amplified and thus any effect of extraneous light falling upon the surface 16 of sample 18 is minimized. The hardware and circuitry necessary to provide the modulated collimated light and the amplifier tuned to the modulator frequency for amplifying the modulated detector output signal are well known in the art and no further description thereof need be made here.

Operation of the apparatus of the present invention is now described as follows with reference to FIGS. 1, 2 and 3. A sample of pummeled laminate 18 is secured to turntable 30. Motor 38 is activated to cause the sample 18 to rotate at a desired r.p.m.. First arched support 40 is pivoted to a desired angle of incidence from the normal X of pummeled laminate 18. Light source 10 is activated by a power source to emit a collimated beam of light 12a having a desired spot size which is then visually directed to the center of the rotating sample 18. The angle of reflection is determined using simple geometry principles based upon the chosen angle of incidence. The detector 20 is then activated and caused to rotate through an arc corresponding to a predetermined starting and stopping point centered on the angle of reflection, i.e. preferably ±30° on either side of the angle of reflection. The detector measures the intensity of the reflected scattered beam of light 12b at regular degree intervals while traveling through the arc. The measurements are then recorded and plotted to produce an intensity scatter profile such as the intensity scatter profiles depicted in FIGS. 4–8.

TEST RESULTS

Figure 4:
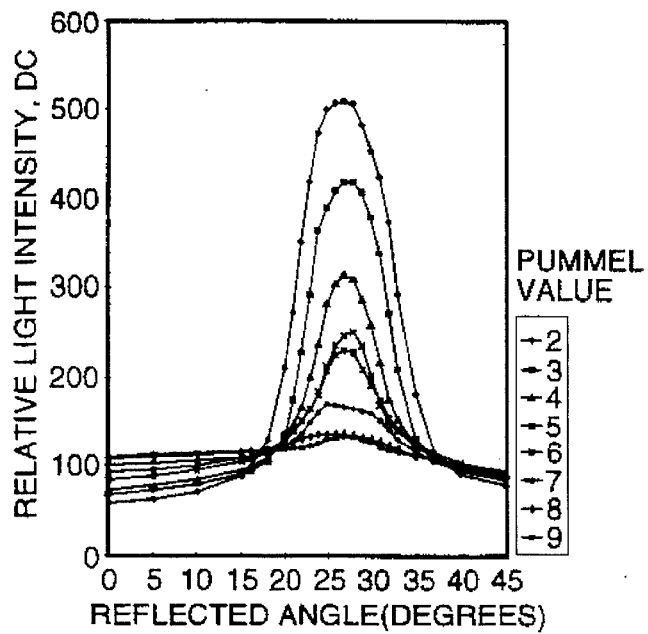
FIGS. 4–8 are scatter intensity profiles of relative light intensity versus the angle of reflection.
Figure 5:
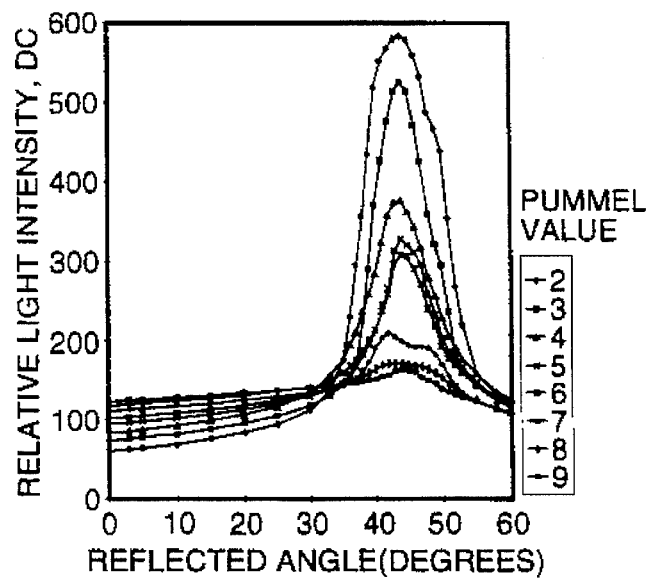
Figure 6:
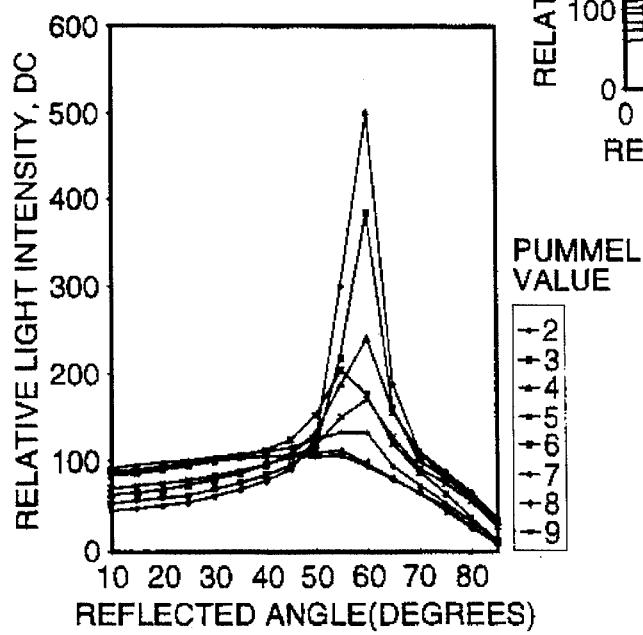
Figure 7:
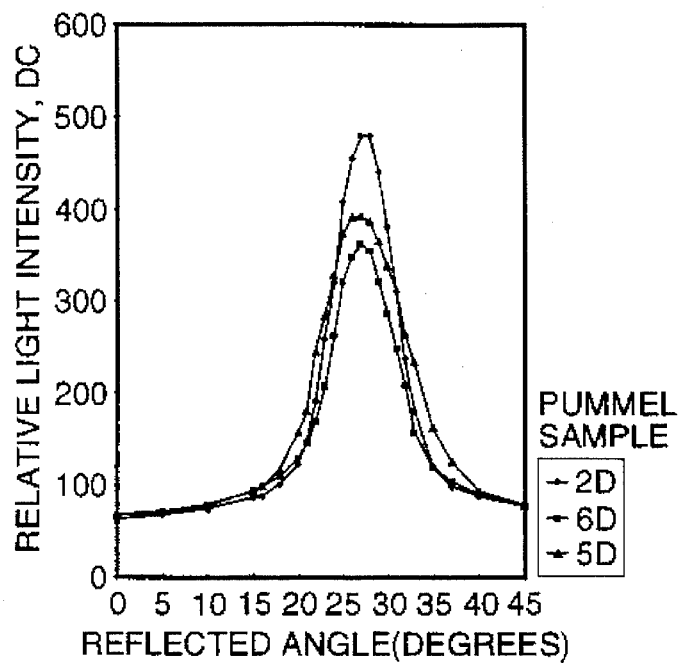
Figure 8:
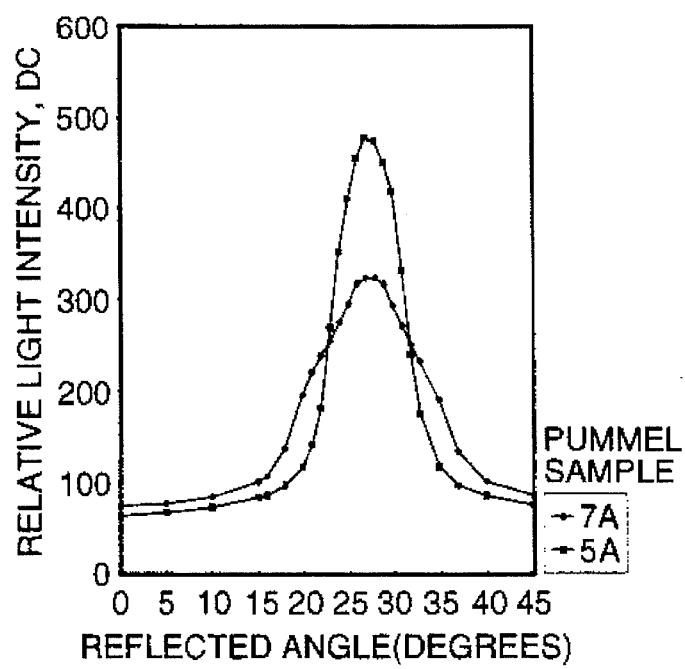

As shown in FIGS. 4, 5 and 6, intensity scatter profiles were determined for a set of Pummel Adhesion Standards ranging from 2 to 9 using the above described method at three different angles of incidence, i.e. 28°, 45° and 60° respectively. As shown in FIGS. 7 and 8, test samples of pummeled glass having visual pummel ratings of 3 and 3.5 were evaluated at a 28° angle of incidence using the same method to evaluate the standards and their intensity scatter profiles determined and plotted. A comparison of the intensity scatter profiles of FIGS. 7 and 8 with the intensity scatter profiles of the standards of FIG. 4 indicates good correlation between the intensity profiles for Standard Adhesion Values 2–4 with the test samples having visual pummel values of 3 and 3.5.

It is to be understood that the embodiments of the invention which have been described are merely illustrative of some applications of the principles of the invention. Numerous modifications may be made by those skilled in the art without departing from the true spirit and scope of the invention.

What is claimed is:

1. A method for determining the quality of adhesion between a glass substrate and a vinyl substrate in a laminated glazing comprising pummeling a sample of the laminated glazing;

rotating the sample;

directing a collimated beam of white light onto the sample at a predetermined angle;

measuring light intensity reflected from the sample; and correlating the measured light intensity with a standard light intensity corresponding to a known pummel adhesion value.

2. The method of claim 1 wherein the sample is rotated at a speed of between about 120 to about 240 r.p.m.

3. The method of claim 1 wherein the predetermined angle is between about 20° and 70°.

4. The method of claim 1 wherein the light intensity reflected from the sample is measured over a several degree interval to produce an intensity scatter profile.

5. The method of claim 1 wherein a computer correlates the measured light intensity with the standard light intensity to assign an adhesion value to the sample.

6. A method for determining the quality of adhesion between a glass substrate and a vinyl substrate in a laminated glazing comprising pummeling a sample of the laminated glazing;

rotating the sample at a speed of between about 120 to about 240 r.p.m.;

directing a collimated beam of white light onto the sample at an angle of between about 20° to about 70°;

measuring light intensity reflected from the sample; and correlating the measured light intensity with a standard light intensity corresponding to a known pummel adhesion value.

7. The method of claim 6 wherein the light intensity reflected from the sample is measured over a several degree interval to produce an intensity scatter profile.

8. The method of claim 6 wherein a computer correlates the measured light intensity with the standard light intensity to assign an adhesion value to the sample.

9. The method of claim 6 wherein the collimated beam of white light is directed onto the sample at an angle of 45°.

10. A method for determining the quality of adhesion between a glass substrate and a vinyl substrate in a laminated glazing comprising pummeling a sample of the laminated glazing;

rotating the sample at a speed of between about 120 to about 240 r.p.m.;

directing a collimated beam of white light onto the sample at an angle of about 45°;

measuring light intensity reflected from the sample over a several degree interval to produce an intensity scatter profile; and computer correlating the measured light intensity with a standard light intensity corresponding to a known pummel adhesion value to assign an adhesion value to the sample.

* * * * *